(12) United States Patent
Watanabe et al.

(10) Patent No.: US 6,762,062 B2
(45) Date of Patent: Jul. 13, 2004

(54) METHOD OF DETERMINING CHOLESTEROL AND SENSOR APPLICABLE TO THE SAME

(75) Inventors: Motokazu Watanabe, Katano (JP); Toshihiko Yoshioka, Hirakata (JP); Shiro Nankai, Hirakata (JP)

(73) Assignee: Matsushita Electric Industrial Co., Ltd., Osaka-fu (JP)

( * ) Notice: Subject to any disclaimer, the term of this patent is extended or adjusted under 35 U.S.C. 154(b) by 0 days.

(21) Appl. No.: 09/961,930

(22) Filed: Sep. 24, 2001

(65) Prior Publication Data

US 2002/0025584 A1 Feb. 28, 2002

Related U.S. Application Data

(63) Continuation of application No. 09/492,979, filed on Jan. 27, 2000, now Pat. No. 6,383,819.

(30) Foreign Application Priority Data

Jan. 27, 1999 (JP) .......................................... 11-018164

(51) Int. Cl.[7] ...................... G01N 33/53; G01N 33/543; G01N 1/18; G01N 33/92; C12Q 1/60

(52) U.S. Cl. ............................... 436/518; 435/4; 435/6; 435/7.1; 435/7.9; 435/7.92; 435/11; 435/174; 435/176; 435/177; 435/287.1; 435/287.2; 435/287.3; 435/288.4; 435/288.5; 435/803; 435/817; 435/25; 435/814; 435/962; 436/71; 436/149; 436/150; 436/177; 436/178; 436/524; 436/528; 436/532; 436/806; 436/815; 436/824; 436/539; 436/825; 422/68.1; 422/82.01; 422/50

(58) Field of Search .......................... 435/4, 6, 7.1, 7.9, 435/7.92, 11, 174, 176, 177, 287.1–287.3, 288.4–288.5, 803, 817, 25, 814, 962, 973; 436/149, 150, 518, 524, 528, 532, 806, 815, 71, 177, 178, 824, 539, 825; 422/68.1, 82.01, 50

(56) References Cited

U.S. PATENT DOCUMENTS 3,957,583 A * 5/1976 Gibson et al. ................ 422/55

(List continued on next page.)

FOREIGN PATENT DOCUMENTS

EP 0 698 791 A1 9/1995

(List continued on next page.)

OTHER PUBLICATIONS

Okada, Masahiko, et al., Low–density lipoprotein cholesterol can be chemically measured: A new superior method, *j. Lab. Clim. Med.*, vol. 132, No. 3, pp. 195–201 (1998).

(List continued on next page.)

*Primary Examiner*—Long Le
*Assistant Examiner*—Kartic Padmanabhan
(74) *Attorney, Agent, or Firm*—Akin, Gump Strauss Hauer & Feld, L.L.P.

(57) ABSTRACT

The present disclosure relates to a method for determining cholesterol in low density lipoprotein comprising the steps of (a) measuring total cholesterol level in a sample containing at least high density lipoprotein, low density lipoprotein, very low density lipoprotein and chylomicron, and (b) measuring cholesterol levels in the high density lipoprotein, very low density lipoprotein and chylomicron in the sample, wherein the cholesterol level in the low density lipoprotein is determined by subtracting a value obtained in the step (b) from a value obtained in the step (a). The present invention enables concurrent determination of cholesterol level in low density lipoprotein and total cholesterol level, facilitating acquisition of two types of biological information at a time.

6 Claims, 5 Drawing Sheets

U.S. PATENT DOCUMENTS

| | | | |
|---|---|---|---|
| 4,110,077 A | | 8/1978 | Klein et al. |
| 4,118,280 A | * | 10/1978 | Charles et al. ............... 250/328 |
| 4,185,963 A | | 1/1980 | Heuck |
| 4,190,628 A | * | 2/1980 | Sears ......................... 422/61 |
| 4,414,326 A | | 11/1983 | Goldberg |
| 4,474,887 A | * | 10/1984 | Maier et al. .................. 436/71 |
| 4,569,917 A | | 2/1986 | Maier et al. |
| 4,576,927 A | * | 3/1986 | Kuroda et al. ............... 502/402 |
| 4,746,605 A | | 5/1988 | Kerscher et al. |
| 4,923,439 A | * | 5/1990 | Seidel et al. .................... 604/6 |
| 5,078,853 A | | 1/1992 | Manning et al. |
| 5,187,010 A | | 2/1993 | Parham et al. |
| 5,213,965 A | | 5/1993 | Jones |
| 5,290,703 A | | 3/1994 | Hsu et al. |
| 5,385,828 A | | 1/1995 | Aufenanger |
| 5,401,466 A | | 3/1995 | Foltz et al. |
| 5,407,836 A | | 4/1995 | Ziegenhorn et al. |
| 5,417,863 A | * | 5/1995 | Varady et al. ............... 210/635 |
| 5,573,919 A | * | 11/1996 | Kearns et al. ............... 435/7.9 |
| 5,736,406 A | | 4/1998 | Miyauchi et al. |
| 5,773,304 A | * | 6/1998 | Hino et al. .................. 436/174 |
| 5,792,619 A | | 8/1998 | Mizoguchi |
| 5,795,786 A | | 8/1998 | Boos et al. |
| 5,804,450 A | | 9/1998 | Karl |
| 5,807,696 A | * | 9/1998 | Miyauchi et al. ............. 435/11 |
| 5,814,472 A | | 9/1998 | Miki et al. |
| 5,846,396 A | * | 12/1998 | Zanzucchi et al. .......... 204/601 |
| 5,879,901 A | | 3/1999 | Futatsugi et al. |
| 5,885,788 A | | 3/1999 | Miki et al. |
| 5,888,827 A | * | 3/1999 | Kayahara et al. ............. 436/71 |
| 5,971,158 A | * | 10/1999 | Yager et al. ................. 209/155 |
| 6,002,475 A | * | 12/1999 | Boyd et al. .................. 356/246 |
| 6,057,118 A | * | 5/2000 | Nakamura et al. ............. 435/11 |
| 6,071,392 A | | 6/2000 | Yamomoto et al. |
| 6,117,289 A | * | 9/2000 | Yamamoto et al. ......... 204/403 |
| 6,331,439 B1 | * | 12/2001 | Cherukuri et al. .......... 436/174 |
| 6,429,025 B1 | * | 8/2002 | Parce et al. .................. 436/514 |

FOREIGN PATENT DOCUMENTS

| | | |
|---|---|---|
| EP | 0 763 741 A1 | 3/1997 |
| EP | 0 794 429 A1 | 9/1997 |
| JP | 57-163500 | 10/1982 |
| JP | 06-102276 | 4/1994 |
| JP | 08-201393 | 8/1996 |
| JP | 09-297121 | 11/1997 |
| JP | 1003888 A | 2/1998 |
| JP | 10 038888 A | 2/1998 |
| WO | WO 79/00306 | 5/1979 |
| WO | WO 90/04416 | 5/1990 |
| WO | WO 93/18067 | 9/1993 |
| WO | WO 94/07146 | 3/1994 |
| WO | WO 94/23302 | 10/1994 |
| WO | WO 96/04556 | 2/1996 |

OTHER PUBLICATIONS

Martinez, et al., "Lipoprotein (a) and other risk factors in children with insulin–dependent diabetes mellitus and children without diabetes", *Diabete & Metabolisme.*, vol. 20, No. 6, pp. 522–525 (1994) (France).

Sugiuchi et al., Homogeneous assay for measuring low–density lipoprotein cholesterol in serum with triblock copolymer and alpha–cyclodextrin sulfate, *Clinical Chemistry*, vol. 44, No. 3, pp. 522–531 (1998).

* cited by examiner

F I G. 3
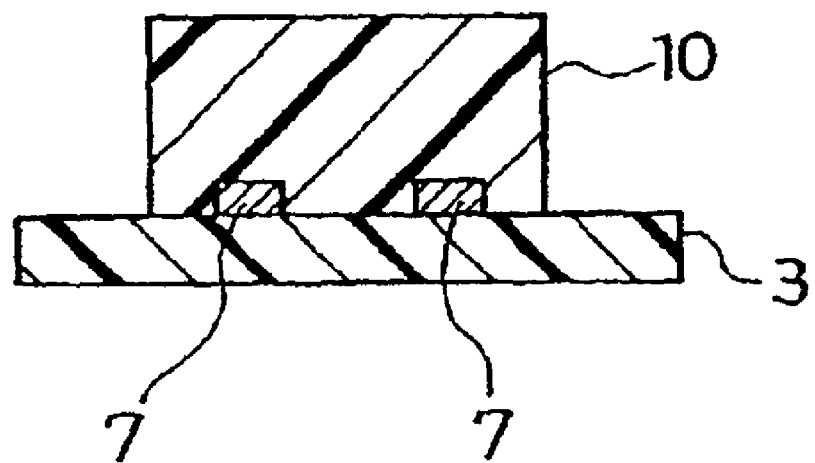

METHOD OF DETERMINING CHOLESTEROL AND SENSOR APPLICABLE TO THE SAME

CROSS REFERENCE TO RELATED APPLICATION

This application is a CON of prior U.S. application Ser. No. 09/492,979, filed Jan. 27, 2000, now U.S. Pat. No. 6,383,819.

BACKGROUND OF THE INVENTION

The present invention relates to a method for determining cholesterol in low density lipoprotein in a sample such as blood, serum and plasma.

A conventional method for determining cholesterol in low density lipoprotein has been based on fractionation using ultracentrifugation. This method, however, has drawbacks of requiring a particular device and taking much time for measurement.

A general method for determining cholesterol without ultracentrifugation is a method which measures total cholesterol level in a sample, cholesterol levels in high density lipoprotein, and triglyceride level individually to calculate cholesterol level in low density lipoprotein using known Friedewald equation. However, this method also has a problem of poor reliability in terms of reproducibility and accuracy if the sample contains much triglyceride.

Recently, a further method for determining cholesterol in low density lipoprotein without requiring a triglyceride value has been proposed in Japanese Laid-Open Patent Publication No. Hei 10-38888; the method comprises step (a) and step (b) wherein the step (a), extinguishes cholesterol contained in high density lipoprotein, very low density lipoprotein and chylomicron of a sample and the step (b) determines cholesterol level in low density lipoprotein. However, since this method determines cholesterol level from the intensity of coloring of a dye, when blood is the sample, the procedure of extinguishing cholesterol is susceptible to an effect of blood concentration (=hematocrit value) because the original sample is already colored. This method has another drawback of laborious procedure due to requirement of individual reagents for the step (a) and step (b), and addition of each reagent to a sample at different time.

An object of the present invention is to provide a method for determining cholesterol in low density lipoprotein only by a single introduction of a sample, from which the above-mentioned drawbacks and disadvantages inherent to the conventional method for determining cholesterol based on the intensity of coloring of a dye, that is, susceptibility to the effect of blood concentration and laborious procedure is excluded.

BRIEF SUMMARY OF THE INVENTION

The present invention for solving the above-mentioned problems relates to a method for determining or quatitating cholesterol in low density lipoprotein comprising the steps of (a) measuring total cholesterol level in a sample containing at least high density lipoprotein, low density lipoprotein, very low density lipoprotein and chylomicron, and (b) measuring cholesterol levels in the high density lipoprotein, very low density lipoprotein and chylomicron in the sample, wherein a cholesterol level in the low density lipoprotein is determined by subtracting a value obtained in the step (b) from a value obtained in the step (a).

In a preferred mode of the present invention, the step (a) and the step (b) are performed at the same time.

In another preferred mode of the present invention, in at least one of the step (a) and the step (b), cholesterol is reacted with a cholesterol specific enzyme and an electron mediator, and then electrochemically oxidizes a resulting reduced electron mediator to determine cholesterol level based on an oxidation current value as obtained.

In still another preferred mode of the present invention, the step (b) may also include a procedure to precipitate the low density lipoprotein. It is particularly desirable to precipitate the low density lipoprotein with the use of an antibody against the low density lipoprotein, heparin hydroxide, acylated heparin hydroxide, glucosaminoglycan sulfate, polysaccharide sulfate, lectin, or polyanion/divalent cation.

The polyanion/divalent cation is preferably polyanethole sulfonate/divalent cation, phosphotungstate/magnesium ion, or dextran sulfate/magnesium ion.

In a further preferred mode of the present invention, the step (b) may include a procedure to adsorb the low density lipoprotein onto a carrier containing a functional group that adsorb the low density lipoprotein. As the functional group, there may be exemplified carboxyl group, a silanol group, a phosphonic acid group and/or sulfonic acid group.

In a still further preferred mode of the present invention, the step (b) determines cholesterol level in the presence of N-(2-hydroxy-3-sulfopropyl)-3,5-dimethoxyaniline, a magnesium ion, a polyalkyl oxide derivative having an HLB value between 13 and 15, and a pH buffer.

The present invention also relates to a sensor applicable to the above-mentioned method for determining cholesterol, the sensor comprising a sample supply unit composed of a sample holder, two reaction wells, and two channels connecting the sample holder with each of the two reaction wells, wherein a connecting position of both of the two channels with the sample holder is at the same height or level in order that excess overflowing sample from the sample holder can outpour into the two channels at the same time.

The present invention enables concurrent determination of total cholesterol level in a sample and cholesterol levels in high density lipoprotein, very low density lipoprotein and chylomicron in the sample, as well as determination of cholesterol level in low density lipoprotein, by a single introduction of the sample.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 3 is a schematic cross-sectional view illustrating reaction wells of one embodiment of the sensor in accordance with the present invention.

DETAILED DESCRIPTION OF THE INVENTION

Figure 1:
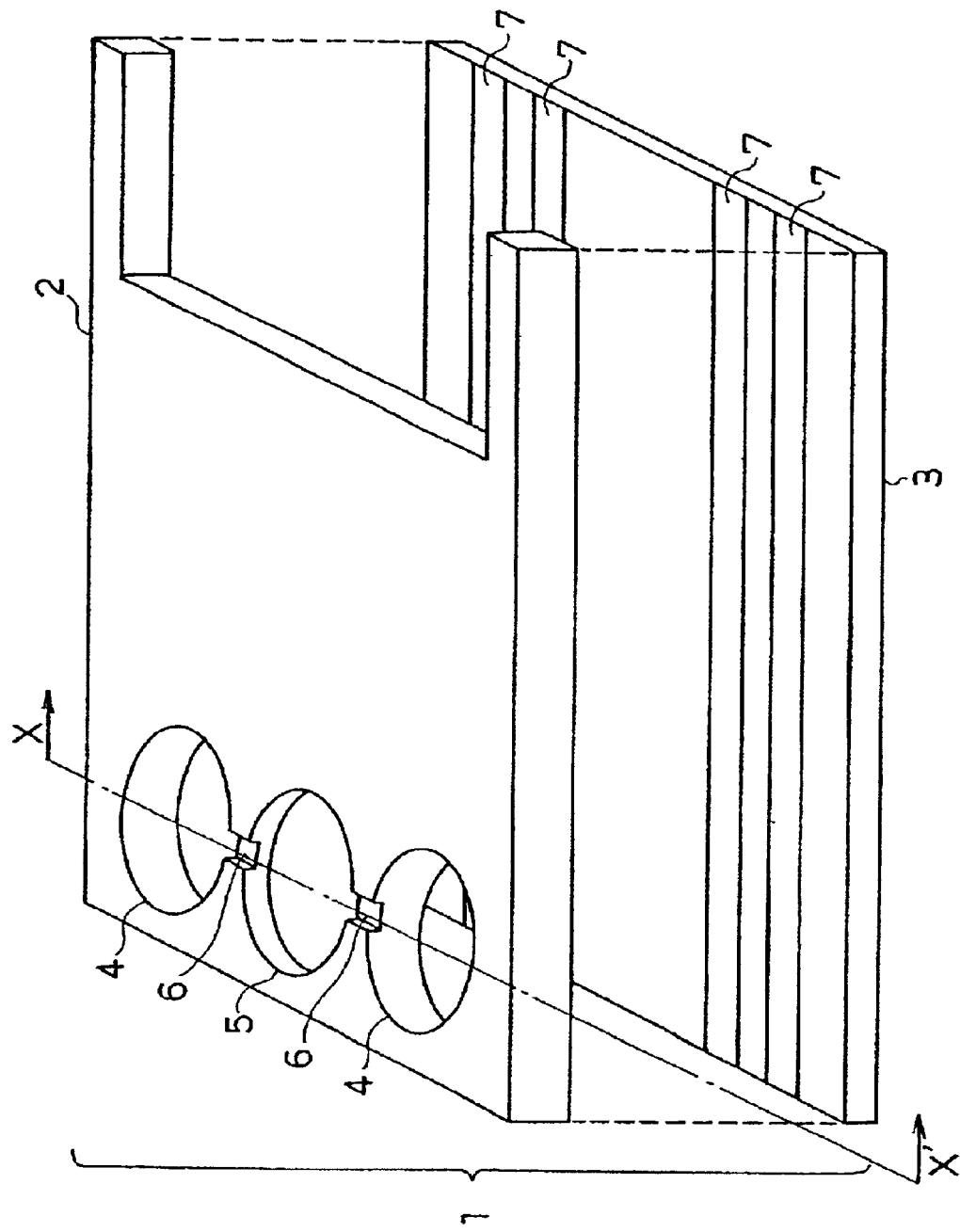
FIG. 1 is an exploded perspective view of one example of a sensor applicable to the method for determining cholesterol in accordance with the present invention.

As discussed above, the present invention comprises the steps of (a) measuring total cholesterol level in a sample containing high density lipoprotein, low density lipoprotein, very low density lipoprotein and chylomicron, and (b) measuring cholesterol levels in the high density lipoprotein, very low density lipoprotein and chylomicron in the sample, wherein a cholesterol level in the low density lipoprotein is determined by subtracting a value obtained in the step (b) from a value obtained in the step (a).

First, the step (a) will be described.

The step (a) in accordance with the present invention measures total cholesterol level in a sample. The sample referred to in the present invention does encompass those containing high density lipoprotein, low density lipoprotein, very low density lipoprotein, and chylomicron, more specifically blood, serum and plasma, for example. Particularly, since the present invention does not measure absorbancy, cholesterol level in low density lipoprotein can be determined even when the sample is blood, or turbid serum or plasma.

Determination of total cholesterol level in the step (a) may be carried out according to a conventionally known method; however, since the present invention enables accurate measurement of cholesterol even in a colored sample such as blood, the use of, for example, a method which reacts cholesterol with a cholesterol specific enzyme in the presence of an electron mediator to reduce the electron mediator by enzyme reaction and then electrochemically oxidizes the reduced electron mediator to obtain an oxidation current value to determine cholesterol level is preferred.

As the enzyme, electron mediator and electrochemical oxidation method to be applied here, conventionally known ones may be employed.

Next, the step (b) will be described.

The step (b) measures cholesterol levels in only high density lipoprotein, very low density lipoprotein and chylomicron in the sample. In other words, of the high density lipoprotein, low density lipoprotein, very low density lipoprotein and chylomicron in the sample, cholesterol contained in only the high density lipoprotein, very low density lipoprotein and chylomicron, excluding the low density lipoprotein, is selectively determined.

Here, the step (b) in accordance with the present invention can be performed by a step (b-1) where cholesterol levels in high density lipoprotein, very low density lipoprotein and chylomicron are determined after removing low density lipoprotein in the sample, or, otherwise, a step (b-2) where cholesterol levels in only high density lipoprotein, very low density lipoprotein and chylomicron are determined without removing low density lipoprotein in the sample.

First, the step (b-1) will be described.

The step (b-1) may be exemplified as a step of precipitating low density lipoprotein or a step of adsorbing low density lipoprotein onto an adsorbent.

In the step of precipitating low density lipoprotein, the low density lipoprotein may be precipitated with the use of an antibody against the low density lipoprotein, heparin hydroxide, acylated heparin hydroxide, glucosaminoglycan sulfate, polysaccharide sulfate, lectin, or polyanion/divalent cation, for example. Among them, the use of antibody against the low density lipoprotein is desirable because of its high specificity to low density lipoprotein.

Preferable polyanion/divalent cation is polyanethole sulfonate/divalent cation, phosphotungstate/magnesium ion, or dextran sulfate/magnesium ion.

Next, in the step of adsorbing low density lipoprotein onto an adsorbent, the low density lipoprotein may be adsorbed onto a carrier containing a functional group that adsorb the low density lipoprotein. The carrier is preferably non-water soluble. As the functional group, there are preferably carboxyl group, sulfonic acid group, a silanol group and phosphonic acid group because they are higher in adsorbing ability. These functional group is so-colled anion type.

Among the carriers, the use of silica is desirable because it allows to vary a thickness of layer freely with ease.

Also, as the carrier, there may be employed a filter such as paper filter or glass filter and a fiber such as one made of polysulfonic acid.

In concrete, a non-water soluble carrier having a silicon resin, a polyacrylic acid, a polymethacrylic acid, a polyvinyl sulfonic acid, polymaleic acid, a polyfumaric acid or polyvinyl alcohol sulfate coated or combined on the surface may be used. When the polyvinyl alcohol sulfate is used, it may be combined to the non-water soluble carrier via glutardialdehyde.

Also, a polysulfonate fiber containing a polyacrylic acid may be preferably used. Such fiber may be obtained by copolymerizing a sulfonate and a acrylester sulfone when forming the polysulfonate fiber. As the polysulfonate fiber, Astrel available from 3M, Victrex available from ICI and Radel available from Amoco may be preferably used.

The step (b-1) has an advantage that cholesterol level can be determined with an identical method to the step (a), because it removes low density lipoprotein.

Next, the step (b-2) will be described.

The step (b-2) measures only cholesterol levels in the high density lipoprotein, very low density lipoprotein and chylomicron without removing low density lipoprotein.

This step requires chemical treatment of the sample in order to prevent only the low density lipoprotein from reacting with the enzyme.

For example, it is preferable to measure cholesterol levels in the presence of N-(2-hydroxy-3-sulfopropyl)-3, 5-dimethoxyaniline, a magnesium ion, a polyalkyl oxide derivative having an HLB value between 13 and 15 exemplified as polyoxyethylene phenyl ether, and a pH buffer, because maximal reactivity of the enzyme with the high density lipoprotein, very low density lipoprotein and chylomicron can be obtained on one hand and minimal reactivity of the enzyme with the low density lipoprotein on the other hand.

Here, the HLB value is a variable parameter depending on the nature of hydrophilic group and hydrophobic group of a surfactant and their ratio; the greater the HLB value, the greater the hydrophilicity. Particularly, the polyalkyl oxide derivative having an HLB value between 13 and 15 is known to destroy a structure of lipoprotein of the high density lipoprotein, very low density lipoprotein and chylomicron and renders cholesterol and cholesterol ester which are constituents of lipoprotein soluble (see Okada et al., J. Lab. Clin. Med. (1998) 132, 195).

In the present invention, it is also desirable to perform the step (a) and the step (b) concurrently, because this proceeds the step (a) and the step (b) at the same time by a single introduction of the sample, thus producing an effect of eliminating a need to supply reagents subsequently.

If this is the case, as mentioned before, it is preferred that at measurement of cholesterol level, at least one of the step (a) and the step (b), preferably the both steps react cholesterol with the cholesterol specific enzyme and the electron mediator, and then electrochemically oxidize the resulting reduced electron mediator to determine the cholesterol level based on an oxidation current value as obtained.

Figure 7:
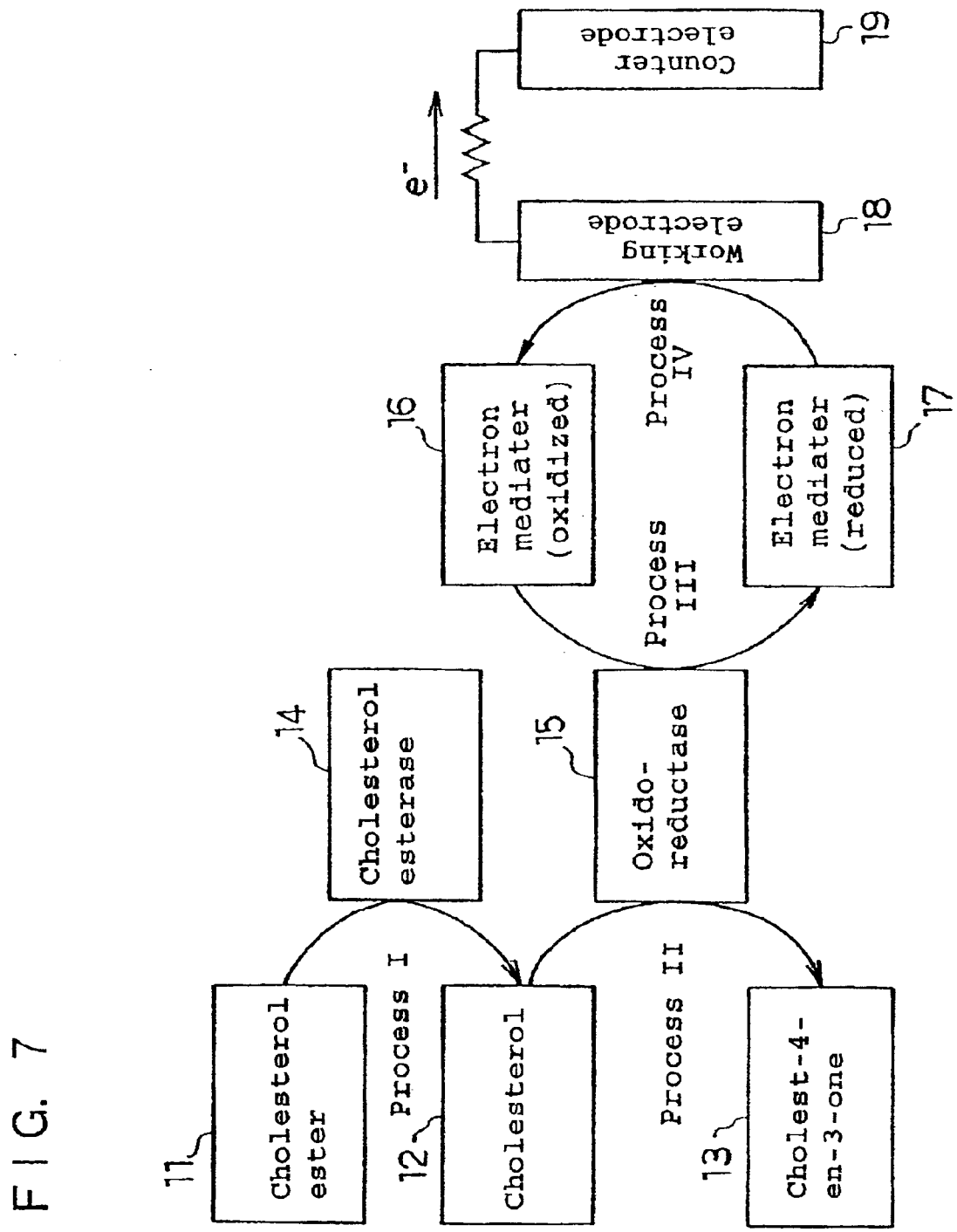
FIG. 7 is a flow chart for explaining a reaction principle in determination of cholesterol concentration.

Now, a principle of reaction in determining cholesterol will be described referring to FIG. 7.

Most cholesterol is present in the lipoprotein of the sample in the form of cholesterol ester in which fatty acid and ester are bonded to each other. Therefore, cholesterol ester 11 is first deesterified into cholesterol 12 using cholesterol esterase 14 (process I).

Subsequently, the cholesterol 12 is oxidized using an oxidoreductase 15 (process II). This oxidation reaction accompanies reduction of an electron mediator 16 at the same time (process III).

Then, a voltage is applied between a working electrode 18 and a counter electrode 19 to oxidize a resulting reduced form electron mediator 17 on the working electrode 18 (process IV). A current flowing in the process IV is then to be measured. A current value at that time depends on a concentration of electron mediator (reduced form) and a concentration of a reduced form electron mediator depends on a concentration of cholesterol. Therefore, the cholesterol level can be obtained by simple measurement of a current flowing between the working electrode 18 and the counter electrode 19. Although a solid enzyme layer is used here, a liquid enzyme layer may also be used.

Next, the present invention also relates to a sensor for performing the quantitative method as explained above based on the above principle. The sensor in accordance with the present invention relates to a sensor comprising a sample supply unit composed of a sample holder, two reaction wells, and two channels connecting the sample holder with each of the two reaction wells, wherein a position of both of the two channels connecting with the sample holder is at the same height in order that excess overflowing sample from the sample holder can flow out into the two channels at the same time.

In the following, the present invention will be described by way of concrete embodiments of the sensor applied to the above-mentioned method for determining cholesterol referring to the drawings, in order to facilitate understanding of the present invention.

Embodiment 1

FIG. 1 shows an exploded perspective view of one example of a sensor applicable to the method for determining cholesterol in accordance with the present invention.

The sensor applying the determining method comprises a sample supply unit composed of a sample holder, two reaction wells, and two channels connecting the sample holder with each of the two reaction wells, wherein a connecting position of both of the two channels with the sample holder is at the same height. This structure enables concurrent outpouring of excess overflowing sample from the sample holder into the two channels.

In FIG. 1, a sensor 1 comprises a cover 2 and a base plate 3. The cover 2 has two reaction wells 4 and a sample holder 5, wherein the sample holder 5 is connected to each of the two reaction wells 4 via channels 6. The reaction wells 4 are penetrating the cover 2 and can function as vessels when the cover 2 is bonded to the base plate 3. The sample holder 5 does not pass through the cover 2, which configuration enables arrival of a sample at the reaction wells 4 after passing through the channels 6 upon supply of a sufficient amount of sample to the sample holder.

The present invention does not limit a material for the cover 2 and the base plate 3 to a particular one and any material having sufficient rigidity and electrical insulation may be used. Examples of preferred applicable materials include thermoplastic resins such as polyethylene, polystyrene, polyvinyl chloride, polyamide and saturated polyester resin, and thermosetting resins such as urea resin, melamine resin, phenolic resin, epoxy resin and unsaturated polyester resin. Of them, polyethylene terephthalate which has excellent adhesiveness to a below-described electrode material is used preferably.

The base plate 3 is formed thereon with electrodes 7. The present invention does not also limit a method for forming the electrode to a particular one and the electrode may be formed by, for example, screen printing a carbon paste on the base plate or, otherwise, vapor-depositing or sputtering palladium on the base plate.

Figure 2:
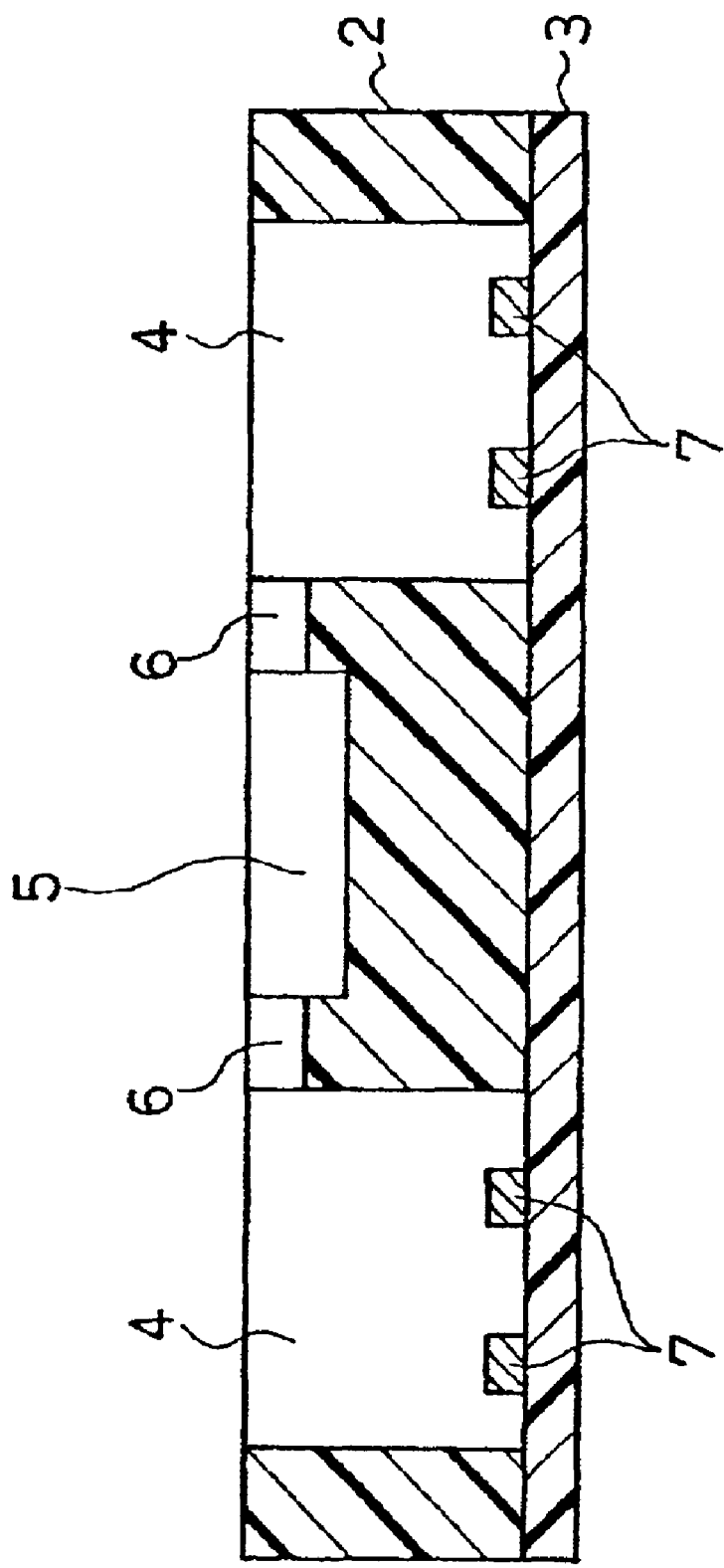
FIG. 2 is a cross-sectional view of a sample supply unit taken on an X–X' line of FIG. 1.

FIG. 2 shows a cross-sectional view of a sample supply unit taken on an X–X' line of FIG. 1 which connects the cover 2, the reaction wells 4 and the sample holder 5. The sample supply unit comprises the sample holder 5, the two reaction wells 4 and the two channels 6 connecting the sample holder 5 with each of the two reaction wells 4. Since a position of both of the two channels 6 connecting with the sample holder 5 is at the same height, excess overflowing sample from the sample holder 5 can outpour into the two channels 6 at the same time.

As shown in FIG. 2, the sensor in accordance with the present invention has a design that the electrodes 7 can be located inside each of the reaction wells 7 when the cover 2 is placed over the base plate 3. One reaction well is provided with a pair of electrodes.

One of the electrodes is used as a working electrode and the other as a counter electrode.

One of the reaction wells contains a reagent for measurement of total cholesterol level (not shown) and the other another reagent for measurement of cholesterol levels in high density lipoprotein, very low density lipoprotein and chylomicron (not shown). The reagents may be liquid or solid.

In the present embodiment, although the reaction well for measurement of total cholesterol level and the reaction well for measurement of cholesterol levels in high density lipoprotein, very low density lipoprotein and chylomicron are disposed inside the same cover but they may be disposed individually inside a different cover.

As mentioned before, the total cholesterol is determined simultaneously with the cholesterol in high density lipoprotein, very low density lipoprotein and chylomicron but the former may be determined at different timing from the latter.

Although there is a hypothesis that cholesterol level in low density lipoprotein is more significant than total cholesterol level (Masahiko Okada, Jap. J. Clin. Lab. Automation (1998) 3, 177), periodic measurement of total cholesterol level is desired if a reductase inhibitor hMG-CoA which is a drug that lowers cholesterol level is prescribed to. Embodiment 1 of the present invention has an advantage that since it allows concurrent quantitation of the total cholesterol with the cholesterol in low density lipoprotein, two different kinds of useful information can be obtained at a time.

Embodiment 2

FIG. 3 shows a schematic cross-sectional view illustrating reaction wells of one embodiment of a sensor in accordance with the present invention.

For those reaction wells, the pair of electrodes 7 are formed on the base plate 3. One electrode can be used as a working electrode and the other as a counter electrode. An enzyme layer 10 is formed on the pair of electrodes 7 by drying an aqueous solution of enzymes.

The enzyme layer 10 contains at least cholesterol esterase, an oxidoreductase and an electron mediator. Conventionally known ones may be used for those components; exemplary oxidoreductases include cholesterol oxidase, etc. and exemplary electron mediators include parabenzoquinone, potassium ferricyanide, etc.

The enzyme layer 10 may optionally contain a surfactant in order to facilitate dissolution of lipoprotein cholesterol. When blood is the sample, then it may be exposed to the enzyme layer 10 from above.

Embodiment 2 of the present invention has an advantage that it enables determination of cholesterol in a colored sample such as blood with no interference of the sample.

Embodiment 3

Figure 4:
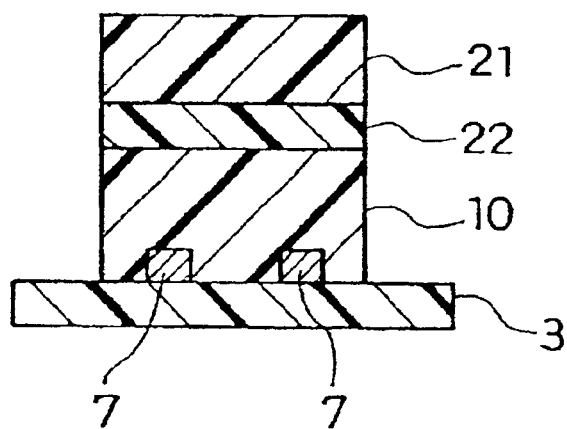
FIG. 4 is a schematic cross-sectional view of reaction wells of another embodiment of the sensor in accordance with the present invention.

FIG. 4 shows a schematic cross-sectional view of reaction wells of another embodiment of a sensor in accordance with the present invention.

Each of the reaction wells is provided with a pair of electrodes and a base plate for measuring cholesterol levels in high density lipoprotein, very low density lipoprotein and chylomicron in a sample.

A pair of electrodes 7 are formed on the base plate 3 and an aqueous solution of enzymes is dried thereon to form the enzyme layer 10 above which a filter 22 is then disposed.

A preferred filter has a pore size between 0.05 and 0.5 $\mu$, and desirable filter materials include glass, paper filter, etc.

A layer of a precipitating agent 21 is formed above the filter 22. Exemplary precipitating agents used here may include an antibody against the low density lipoprotein, heparin hydroxide, acylated heparin hydroxide, glucosaminoglycan sulfate, polysaccharide sulfate, lectin, and polyanion/divalent cation. Furthermore, preferred examples of the polyanion/divalent cation are polyanethole sulfonate/divalent cation, phosphotungstate/magnesium ion, and dextran sulfate/magnesium ion.

When blood or the like is sample, if the sample is exposed to the layer of the precipitating agent 21 from above, then the low density lipoprotein in the sample is aggregated and precipitated. The low density lipoprotein thus precipitated is filtered by the filter 22 located below the layer of the precipitating agent 21, which prevents arrival of the low density lipoprotein at the enzyme layer 10.

The remaining sample which has passed through the filter 22 contains high density lipoprotein, very low density lipoprotein and chylomicron. Upon arrival of the sample which has passed the filter 22 at the enzyme layer 10, the reaction as described above referring to FIG. 7 proceeds and cholesterol in the high density lipoprotein, very low density lipoprotein and chylomicron can be quantitated.

In this embodiment, although the enzyme layer is solid, it may be liquid.

Embodiment 3 in accordance with the present invention has an advantage that a single supply of the sample from above the layer of the precipitating agent enables determination of cholesterol in low density lipoprotein.

Embodiment 4

Figure 5:
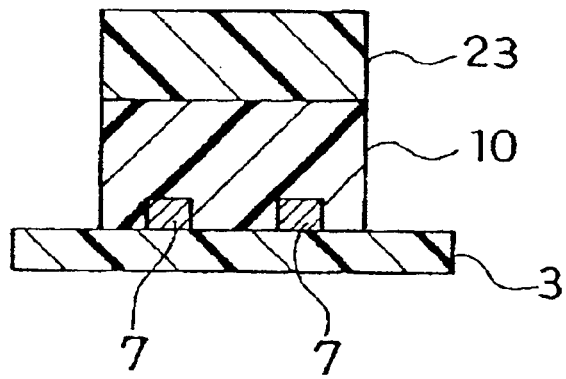
FIG. 5 is a schematic cross-sectional view of reaction wells of still another embodiment of the sensor in accordance with the present invention.

FIG. 5 shows a schematic cross-sectional view of reaction wells of still another embodiment of a sensor in accordance with the present invention.

Embodiment 4 differs from the above Embodiment 3 in that a layer of an adsorbent 23 is formed in place of the filter and the layer of the precipitating agent.

As the adsorbent 23, the above-exemplified silica, polysulfonate fiber containing a polyacrylic acid, silanol group, polyanion group, and polyvinyl alcohol sulfate are preferred. As the polyanion group, the above-exemplified polycarboxyl group, polysulfone group, polyphosphonic group, and polyacrylic group are preferred.

When blood or the like is sample, if the sample is first exposed to the layer of the adsorbent 23, the low density lipoprotein in the sample is adsorbed onto the adsorbent 23 from above, which prevents arrival of the low density lipoprotein at the enzyme layer 10.

The remaining sample which has passed through the layer of the adsorbent 23 and contains high density lipoprotein, very low density lipoprotein and chylomicron arrives at the enzyme layer 10. As a result, the reaction as described above referring to FIG. 7 proceeds at the enzyme layer 10 and cholesterol in the high density lipoprotein, very low density lipoprotein and chylomicron can be quantitated.

Embodiment 4 in accordance with the present invention has an advantage that a single supply of the sample from above the layer of the adsorbent enables quantitation of cholesterol in low density lipoprotein.

Embodiment 5

Figure 6:
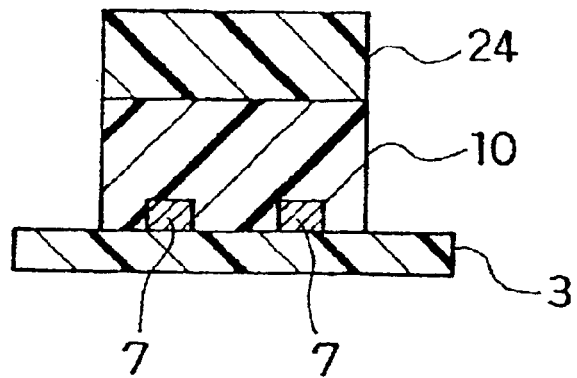
FIG. 6 is a schematic cross-sectional view of reaction wells of still another embodiment of the sensor in accordance with the present invention.

FIG. 6 shows a schematic cross-sectional view of reaction wells of still another embodiment of a sensor in accordance with the present invention.

Embodiment 5 differs from the above Embodiment 4 in that a reagent layer 24 is formed in place of the layer of the adsorbent.

The reagent layer 24 contains the above-exemplified N-(2-hydroxy-3-sulfopropyl)-3,5-dimethoxyaniline, magnesium ion, polyalkyl oxide derivative having an HLB value between 13 and 15, and pH buffer.

Embodiment 5 in accordance with the present invention has an advantage that a single supply of the sample from above the reagent layer enables determination of cholesterol in low density lipoprotein.

As such, the present invention has an advantage that since cholesterol level in low density lipoprotein and total cholesterol level can be determined at the same time, two types of biological information can be obtained at a time; cholesterol level in low density lipoprotein plus total cholesterol level useful in diagnosing hypercholesterolemia, and total cholesterol level useful in determining the efficacy of prescribed drugs.

The present invention also enables determination of cholesterol in low density lipoprotein by a single supply of a sample by simultaneously performing the steps of (a) measuring total cholesterol level in a sample, and (b) measuring cholesterol levels in the high density lipoprotein, very low density lipoprotein, and chylomicron in the sample, and then subtracting a value obtained in the step (b) from a value obtained in the step (a).

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A device for analysis of a cholesterol level in a sample comprising a sample supply unit that comprises:

a sample holder;

a first reaction well and a second reaction well, wherein each reaction well contains an enzyme that reacts with cholesterol, and the second reaction well further contains a reagent selected from a low density lipoprotein (LDL) precipitating reagent, a low density lipoprotein (LDL) adsorbing reagent, and a reagent that prevents a low density lipoprotein (LDL) from reacting with the enzyme;

two channels connecting the sample holder with each of the two reaction wells, wherein a position of both of the two channels connecting with the sample holder is at a same height in order that excess overflowing sample from the sample holder outpours into the two channels.

2. The device of claim 1, wherein each of said two reaction wells comprises a pair of electrodes.

3. The device of claim 1, wherein each of said channels has a form to permit overflow of a sample from the sample holder to each of said channels.

4. The device of claim 1, wherein the low density lipoprotein (LDL) precipitating reagent is selected from the group consisting of an antibody against low density lipoprotein, heparin hydroxide, acylated heparin hydroxide, glucosaminoglycan sulfate, polysaccharide sulfate, lectin, polyanethole sulfonate/divalent cation, phosphotungstate/magnesium ion, and dextran sulfate/magnesium ion.

5. The device of claim 1, wherein the low density lipoprotein (LDL) adsorbing reagent is an adsorbent that comprises a functional group selected from a carboxyl group, a silanol group, a phosphonic acid group, and a sulfonic acid group.

6. The device of claim 1, wherein the reagent that prevents a low density lipoprotein (LDL) from reacting with the enzyme comprises N-(2-hydroxy-3-sulfopropyl)-3,5-dimethoxyaniline, a magnesium ion, a polyalkyl oxide derivative having an HLB value between 13 and 15, and a pH buffer.

* * * * *